(12) United States Patent
Oren et al.

(10) Patent No.: US 10,238,348 B2
(45) Date of Patent: *Mar. 26, 2019

(54) REPRESENTATIVE EMULATION OF ORGAN BEHAVIOR

(71) Applicant: St. Jude Medical International Holding S.à r.l., Luxembourg (LU)

(72) Inventors: Eitan Oren, Haifa (IL); Kobi Segev, Haifa (IL); Avinoam Romano, Kibbutz Ein Dor (IL); Itay Kariv, Haifa (IL); Rohan More, Los Angeles, CA (US); Alex Peleg, Haifa (IL); Alon Izmirli, Ganot Hadar (IL)

(73) Assignee: ST JUDE MEDICAL INTERNATIONAL HOLDING S.À R.L., Luxembourg (LU)

(*) Notice: Subject to any disclaimer, the term of this patent is extended or adjusted under 35 U.S.C. 154(b) by 0 days.

This patent is subject to a terminal disclaimer.

(21) Appl. No.: 15/850,615

(22) Filed: Dec. 21, 2017

(65) Prior Publication Data

US 2018/0228449 A1    Aug. 16, 2018

Related U.S. Application Data

(63) Continuation of application No. 14/188,007, filed on Feb. 24, 2014, now Pat. No. 9,848,832, which is a continuation of application No. PCT/IB2014/059120, filed on Feb. 20, 2014.

(60) Provisional application No. 61/808,047, filed on Apr. 3, 2013, provisional application No. 61/769,613, filed on Feb. 26, 2013, provisional application No. 61/768,025, filed on Feb. 22, 2013.

(51) Int. Cl.
A61B 5/00 (2006.01)
A61B 5/06 (2006.01)

(52) U.S. Cl.
CPC ............ *A61B 5/7425* (2013.01); *A61B 5/064* (2013.01)

(58) Field of Classification Search
USPC .......................................... 382/128
See application file for complete search history.

(56) References Cited

U.S. PATENT DOCUMENTS

| | | |
|---|---|---|
| 5,976,088 A | 11/1999 | Urbano |
| 6,233,476 B1 | 5/2001 | Strommer et al. |
| 6,690,963 B2 | 2/2004 | Ben-Haim et al. |
| 7,197,354 B2 | 3/2007 | Sobe |
| 7,263,397 B2 | 8/2007 | Hauck et al. |
| 7,289,841 B2 | 10/2007 | Johnson et al. |
| 7,386,339 B2 | 6/2008 | Strommer et al. |

(Continued)

FOREIGN PATENT DOCUMENTS

| | | |
|---|---|---|
| DE | 102010022791 A1 | 12/2011 |
| WO | 2012090148 A1 | 7/2012 |

*Primary Examiner* — Ishrat I Sherali
(74) *Attorney, Agent, or Firm* — Dykema Gossett PLLC

(57) ABSTRACT

A method for emulating prerecorded images may comprise acquiring at least one organ timing signal reading representing an activity state of an organ with at least one organ timing signal detector, acquiring a plurality of images with a medical imaging system, associating each of the plurality of images with an organ timing signal reading, removing any of the organ timing signal readings and associated images that are not representative of a normal organ configuration, and outputting a sequence of the representative images for a display.

25 Claims, 7 Drawing Sheets

(56) References Cited

U.S. PATENT DOCUMENTS

| | | | |
|---|---|---|---|
| 7,697,973 B2 | 4/2010 | Strommer et al. | |
| 7,848,789 B2 | 12/2010 | Govari et al. | |
| 8,781,566 B2 | 7/2014 | John et al. | |
| 9,848,832 B2 * | 12/2017 | Oren | A61B 5/064 |
| 2003/0016852 A1 | 1/2003 | Kaufman et al. | |
| 2004/0077941 A1 * | 4/2004 | Reddy | A61B 6/032 |
| | | | 600/428 |
| 2005/0107688 A1 * | 5/2005 | Strommer | A61B 5/0066 |
| | | | 600/424 |
| 2005/0251028 A1 | 11/2005 | Boese et al. | |
| 2006/0058647 A1 * | 3/2006 | Strommer | A61B 5/06 |
| | | | 600/434 |
| 2008/0063137 A1 * | 3/2008 | Hsieh | A61B 5/0464 |
| | | | 378/8 |
| 2011/0158488 A1 * | 6/2011 | Cohen | A61B 6/12 |
| | | | 382/128 |
| 2011/0245651 A1 * | 10/2011 | Nakamura | A61B 5/055 |
| | | | 600/407 |
| 2011/0298793 A1 | 12/2011 | Lauritsch et al. | |
| 2013/0066193 A1 | 3/2013 | Olson et al. | |

\* cited by examiner

REPRESENTATIVE EMULATION OF ORGAN BEHAVIOR

CROSS-REFERENCE TO RELATED APPLICATIONS

This application is a continuation of U.S. application Ser. No. 14/188,007, filed 24 Feb. 2014 ("the '007 application"), which is a continuation of Patent Cooperation Treaty application No. PCT/IB2014/059120, filed 20 Feb. 2014 ("the '120 application"), which claims the benefit of U.S. provisional patent application No. 61/768,025, filed 22 Feb. 2013 ("the '025 application"), U.S. provisional patent application No. 61/769,613, filed 26 Feb. 2013 ("the '613 application"), and U.S. provisional patent application No. 61/808,047, filed 3 Apr. 2013 ("the '047 application"). The '007 application, the '120 application, the '025 application, the '613 application, and the '047 application are all hereby incorporated by reference in their entireties.

BACKGROUND a. Technical Field

The present disclosure relates to medical systems and methods for representing and/or emulating anatomies of patient's behavior. More particularly, the present disclosure relates to a medical imaging system and a method for replaying pre-acquired images (i.e., a cine-loop) taken during imaging, for example, with a fluoroscope.

b. Background Art

During a medical procedure, it is desirable to view the position of one or more medical devices relative to a patient's anatomy (i.e., organs, vasculature, etc.). One known method for viewing the position of a medical device is to continuously image the region of interest of the patient with imaging radiation, e.g., real time fluoroscopy. Ongoing real-time imaging, however, may expose the patient and/or physician to undesirable amounts of imaging radiation.

To reduce the amount of radiation to which a patient and physician are exposed, systems and procedures have been developed for emulating real-time fluoroscopy by playing a loop of pre-recorded images (referred to herein as a "cine-loop"). In general, a physician schedules the start and end period of an operation to capture the loop of images. The cine-loop is then replayed in synchronization with a timing signal (e.g., an organ timing signal), to emulate a display of real-time images.

BRIEF SUMMARY

Devices, systems, and methods for providing and/or outputting a cine-loop may be improved by removing images from the cine-loop that are not representative of a normal configuration (e.g., shape) of the organ. An embodiment of a control unit for a system for displaying looped images, such as a cine-loop, may be configured to be coupled with a medical imaging system. The control unit may comprise a computer-readable memory configured to store instructions and a processor configured to execute the instructions. By executing the instructions, the processor may associate each of a plurality of two dimensional images of an organ acquired from the medical imaging system with a respective activity state of the organ, assess whether one or more of the plurality of two dimensional images is representative of a normal configuration of the organ at the respective activity state, and output, for a display, a set of looped images that comprises each of the plurality of two-dimensional images that is representative of the normal configuration of the organ at the respective activity state and excludes each of the plurality of two-dimensional images that is not representative of the normal configuration of the organ at the respective activity state.

An embodiment of a method for emulating prerecorded images, such as a cine-loop, may comprise acquiring at least one organ timing signal reading representing an activity state of an organ with at least one organ timing signal detector, acquiring a plurality of images with a medical imaging system, associating each of the plurality of images with an organ timing signal reading, removing any of the organ timing signal readings and associated images that are not representative of a normal organ configuration, and outputting a sequence of the representative images for a display.

An embodiment of a system for emulating prerecorded images, such as a cine-loop, may comprise at least one organ timing signal detector, a medical imaging system, and a control unit. The organ timing signal detector may be configured to acquire at least one organ timing signal reading, the organ timing signal reading representing an activity state of an organ. The medical imaging system may be for acquiring a plurality of images. The control unit may be coupled with the organ timing signal detector and with the medical imaging system and may be configured to associate each of the plurality of images with a respective organ timing signal reading. The control unit may be further configured to record an output of the organ timing signal detector and to produce only representative images by analyzing the output and removing any of the organ timing signals readings and the associated images that do not conform to a representative organ state, and further wherein the control unit is configured to send only representative images to a display system by corresponding the associated image with the received organ timing signal reading.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
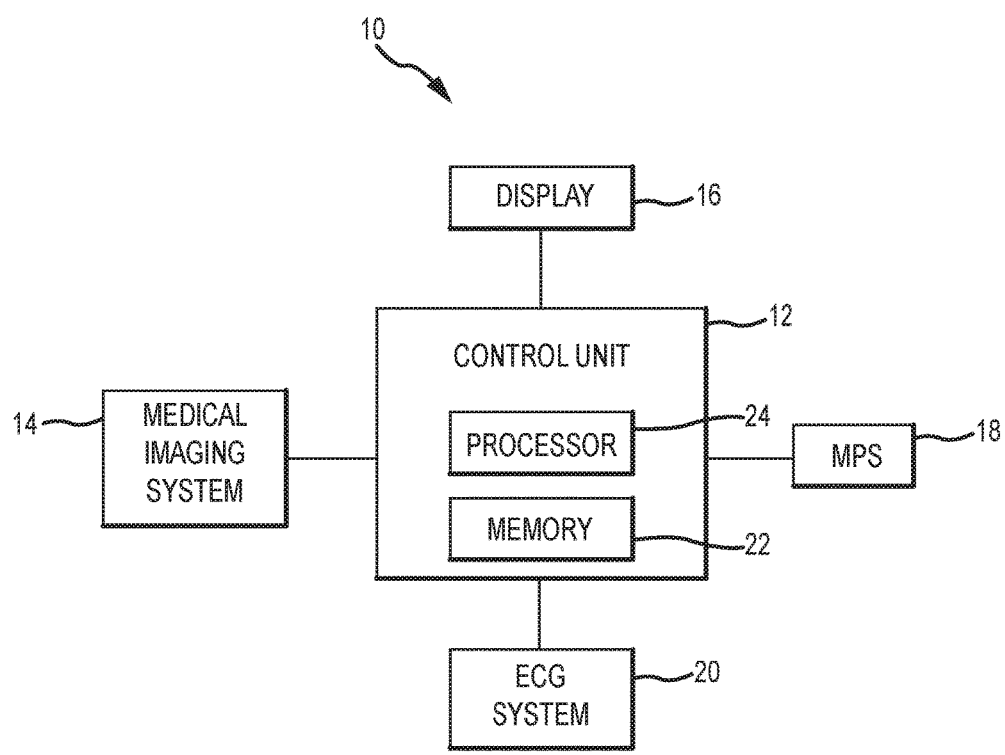
FIG. 1 is a block diagram of a system for emulating prerecorded images of a portion of a patient's body, such as an organ.

Referring now to the figures, in which like reference numerals refer to the same or similar elements in the various views, FIG. 1 is a block diagram view of a system 10 for emulating prerecorded images of a portion of a patient's body, such as an organ, such as the heart. The system 10 may include a control unit 12, a medical imaging system 14, a display 16, a medical device positioning, mapping, and navigation system (which may be referred to herein simply as an MPS) 18, and an organ timing signal system, such as an electrocardiogram (ECG) system 20.

The medical imaging system 14 may comprise, in an embodiment, a fluoroscopy system. The medical imaging system 14 will be described herein with reference to an embodiment in which the medical imaging system is a fluoroscopy system, but the system 10 is not so limited. In embodiments, the medical imaging system 14 may be or may include a fluoroscopy system and/or other imaging modalities including, but not limited to, computed tomography (CT), magnetic resonance imaging (MRI), ultrasound, and other known medical imaging modalities.

The MPS 18 may be provided for visualization, navigation, and/or mapping of internal body structures. The MPS 18 may comprise a magnetic field based localization system such as that based on the MediGuide™ Technology available from St. Jude Medical, Inc. (e.g., as exemplified by U.S. patent application Ser. No. 09/782,528 (issued as U.S. Pat. No. 7,386,339); U.S. patent application Ser. No. 10/873,409 (issued as U.S. Pat. No. 7,197,354) and U.S. patent application Ser. No. 09/314,474 (issued as U.S. Pat. No. 6,233,476), all of which are hereby incorporated by reference in their entireties as though fully set forth herein), the Carto™ visualization and location system available from Biosense Webster, Inc., (e.g., as exemplified by U.S. patent application Ser. No. 08/793,371 (issued as U.S. Pat. No. 6,690,963), hereby incorporated by reference in its entirety as though fully set forth herein), or the Aurora™ system available from Northern Digital Inc. In an embodiment, the MPS 18 may comprise an electrical-impedance based system, such as an EnSite™ Velocity™ system running a version of EnSite™ NavX™ software commercially available from St. Jude Medical, Inc., and as also seen generally by reference to U.S. patent application Ser. No. 10/819,027 (issued as U.S. Pat. No. 7,263,397), hereby incorporated by reference in its entirety as though fully set forth herein. In an embodiment, the MPS 18 may comprise a hybrid magnetic field-impedance based system, such as that shown in U.S. patent application Ser. No. 13/231,284 (published as United States patent application publication No. 2013/0066193), which is hereby incorporated by reference in its entirety as though fully set forth herein, or the Carto™ 3 visualization and location system available from Biosense Webster, Inc. (e.g., as exemplified by U.S. patent application Ser. No. 12/425,778 (issued as U.S. Pat. No. 7,848,789), which is hereby incorporated by reference in its entirety as though fully set forth herein). Some embodiments of an MPS 18 may include a sensor for producing signals indicative of catheter location and/or distal portion orientation information, and can include, for example, one or more electrodes in the case of an impedance-based localization system such as the EnSite™ Velocity™ system running EnSite™ NavX™ software, which electrodes can already exist in some instances, or alternatively, one or more coils (i.e., wire windings) configured to detect one or more characteristics of a low-strength magnetic field, for example, in the case of a magnetic-field based localization system such as one including the MediGuide™ Technology described above.

For ease of description, the remainder of this disclosure will be with respect to an embodiment in which the MPS 18 is a magnetic-field based system, but the systems, methods, and techniques discussed herein are not so limited. Instead, the systems, methods, and techniques discussed herein may also find application with another type of MPS 18, including, but not limited to, those systems and types of systems noted above.

The ECG system 20 may be provided for obtaining and recording an electrocardiogram (i.e., an organ timing signal respective of the heart of a patient). The ECG system 20 may include a number of electrodes placed on the patient's body and a monitor or other controller, as known in the art.

In embodiments, instead of or in addition to the ECG system 20, the system 10 may include another type of organ timing signal detector. For example, the system 10 may include one or more electrodes disposed within the heart and configured to capture a heart timing signal from within the heart, a detector configured to detect a respiratory signal (i.e., an organ timing signal respective of the lungs) and/or an organ timing signal respective of another organ. Furthermore, for ease of description, although the remainder of the disclosure will refer to an embodiment in which the relevant organ is the heart, it should be understood that an organ of interest (e.g., the subject of a medical procedure, one or more images, organ timing signal, etc.) may be a heart and/or another organ or portion of a patient's body.

The control unit 12 may include a non-volatile computer-readable memory 22 and a processor 24. The memory 22 may be configured to store instructions and the processor 24 may be configured to execute those instructions to perform one or more functions and methods described herein.

The control unit 12 may be configured to receive images collected by the medical imaging system 14, an ECG from the ECG system 20 and/or another organ timing signal, and position and orientation information from the MPS 18. The control unit 12 may be configured to, among other things, associate images collected with the medical imaging system 14 with ECG data and with position and orientation information. In an embodiment, the control unit 12 may be configured to associate each image collected with the medical imaging system 14 with an activity state of the heart (e.g., with a portion of a cardiac cycle according to an ECG) and with a position and orientation of the medical imaging system 14. The control unit 12 may use the images to construct a loop of recorded images of the heart (i.e., a cine-loop), that may be played on the display 16 during a medical procedure to replace or supplement real-time imaging with the medical imaging system 14 or another imaging modality or system. The control unit 12 may be further configured to direct or guide collection of images for a cine-loop, as described below.

Figure 2:
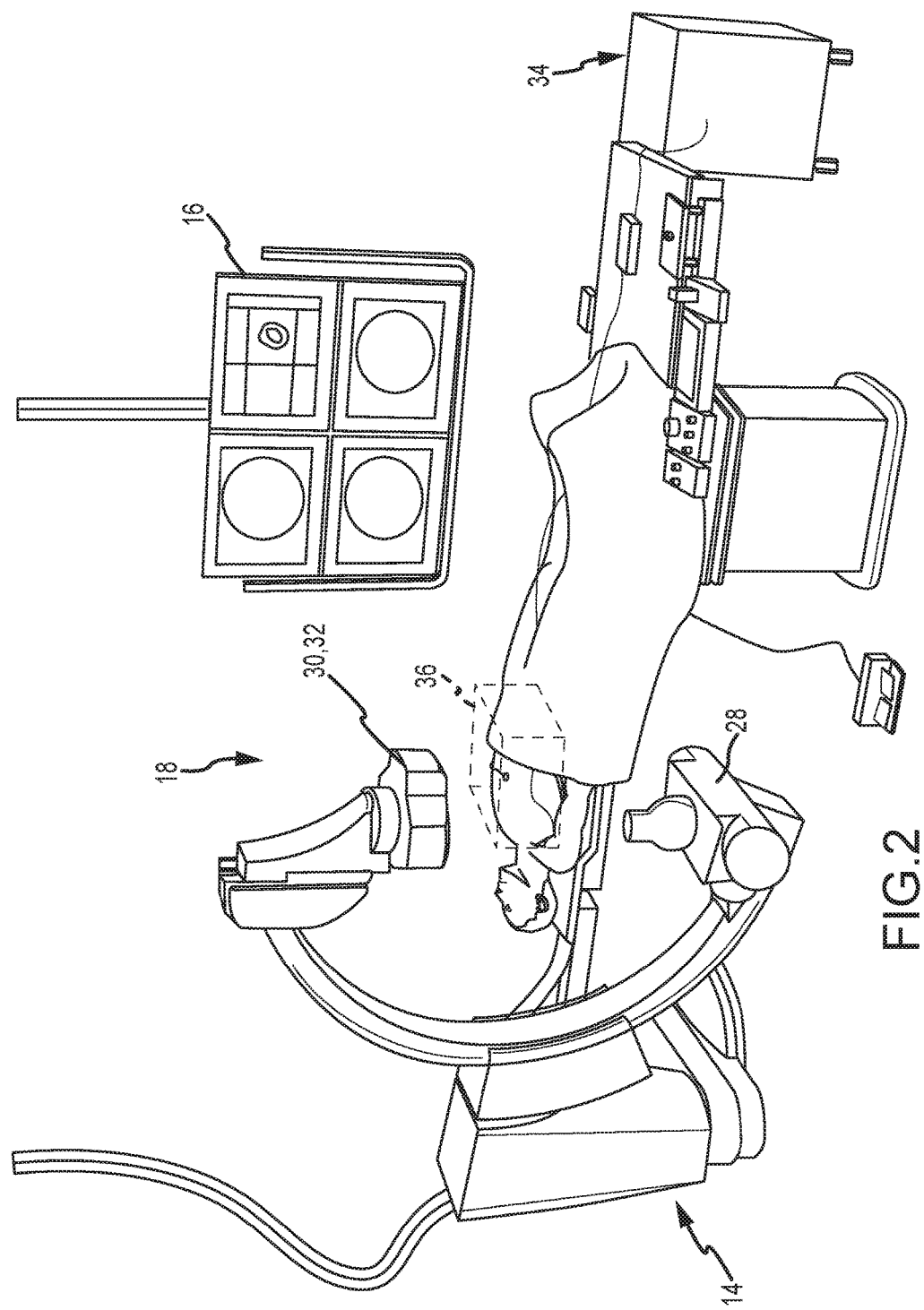
FIG. 2 is a diagrammatic view of an embodiment of a medical device laboratory including an exemplary fluoroscopic imaging system and an exemplary magnetic field-based positioning system.

FIG. 2 is a diagrammatic view of an embodiment of a medical device laboratory including an embodiment of the medical imaging system 14 (shown as a fluoroscopic imaging system) and an embodiment of the MPS 18.

The imaging system 14 may include a C-arm 26, an imaging radiation transmitter 28, and an imaging radiation detector 30. The C-arm 26 may be rotated and/or translated and radiation (i.e., x-ray) may be transmitted from the imaging radiation transmitter 28 to the imaging radiation detector 30 to image an area of interest of a the body of a patient. In an embodiment, the area of interest may be or may include the heart and/or another organ of the patient. The imaging system 14 may provide images to a control unit (e.g., the control unit 12 shown in FIG. 1) for further processing.

With continued reference to FIG. 2, the MPS 18 may include a magnetic transmitter assembly (MTA) 32 and a magnetic processing core 34 for determining position and orientation (P&O) readings. In an embodiment, the processing core 34 may be or may be a part of the control unit 12 of FIG. 1. The MTA 32 may be configured to generate one or more magnetic fields in and around a volume of interest, such as the patient's chest cavity, in a predefined three-dimensional space designated as volume of interest 36 in FIG. 2. Magnetic field sensors coupled with a medical device may be configured to sense one or more characteristics of the magnetic field(s) and, when the sensors are in the volume of interest 36, may each generate a respective signal that is provided to the magnetic processing core 34. The processing core 34 may be responsive to these detected signals and may calculate respective three-dimensional position and orientation (P&O) readings for each magnetic field sensor in the volume of interest 36. Thus, the MPS 18 may enable real-time tracking of each magnetic field sensor in three-dimensional space. The position of the sensors may be shown on the display 16 relative to, for example only, a cine-loop, real-time images obtained from the medical imaging system 14, or a model of the heart or other features of the volume of interest.

Figure 3:
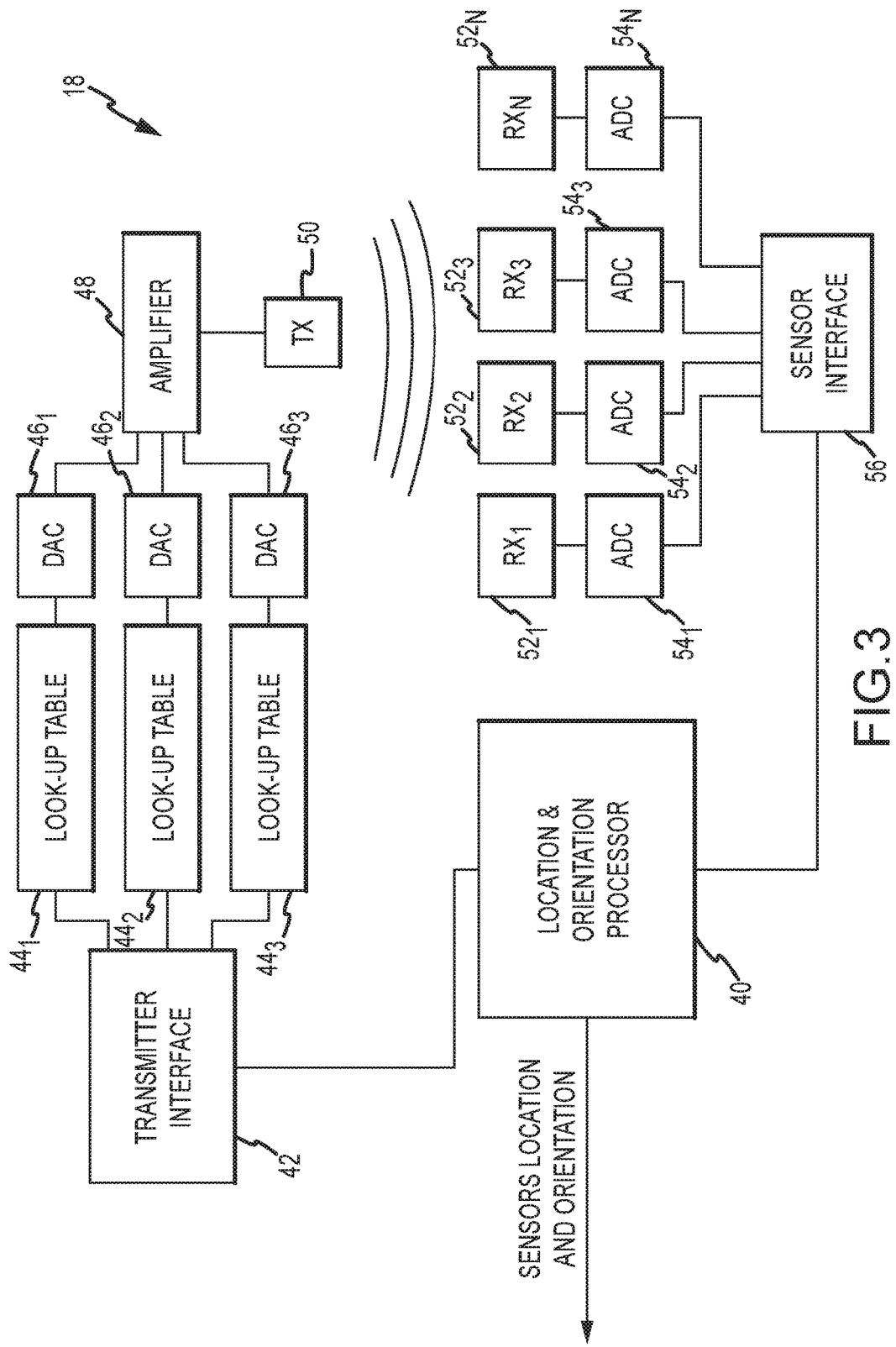
FIG. 3 is a schematic and block diagram view of the magnetic field-based positioning system of FIG. 2.

FIG. 3 is a schematic and block diagram view of the MPS 18. The MPS 18 may include a location and orientation processor 40, a transmitter interface 42, a plurality of look-up table units $44_1$, $44_2$, $44_3$, a plurality of digital to analog converters (DAC) $46_1$, $46_2$, $46_3$, an amplifier 48, a transmitter (marked "TX" in FIG. 3) 50, a plurality of MPS sensors (each marked "RX" in FIG. 3) $52_1$, $52_2$, $52_3$, $52_N$, a plurality of analog to digital converters (ADC) $54_1$, $54_2$, $54_3$, $54_N$, and a sensor interface 56.

The MPS 18 is configured to acquire positioning (localization) data (i.e., position and orientation-P&O) of the MPS sensors $52_1$, $52_2$, $52_3$, $52_N$. For some sensors, the P&O may be expressed with five degrees of freedom as a position (i.e., a coordinate in three axes X, Y and Z) and orientation (i.e., an azimuth and elevation) of the respective sensor $52_1$, $52_2$, $52_3$, $52_N$ in a magnetic field relative to the magnetic field transmitter 50. For other sensors $52_1$, $52_2$, $52_3$, $52_N$, the P&O may be expressed with six degrees of freedom as a position (X, Y, and Z) and orientation (i.e., roll, pitch, and yaw). The P&O may be based on capturing and processing the signals received from a sensor $52_1$, $52_2$, $52_3$, $52_N$ while in the presence of a controlled low-strength AC magnetic field. Accordingly, the sensors $52_1$, $52_2$, $52_3$, $52_N$ may each comprise one or more magnetic field detection coil(s), and it should be understood that variations as to the number of coils, their geometries, spatial relationships, the existence or absence of cores and the like are possible. From an electromagnetic perspective, voltage is induced on a coil residing in a changing magnetic field, as contemplated here. The sensors $52_1$, $52_2$, $52_3$, $52_N$ are thus configured to detect one or more characteristics of the magnetic field(s) in which they are disposed and generate an indicative signal, which is further processed to obtain the P&O thereof. For one example of a sensor, see U.S. patent application Ser. No. 10/873,409 (issued as U.S. Pat. No. 7,197,354), which is hereby incorporated by reference in its entirety.

The transmitter interface 42, DAC units $46_1$, $46_2$, $46_3$, and transmitter 50 are provided to create the controlled low-strength AC magnetic field. The MPS sensors $52_1$, $52_2$, $52_3$, $52_N$, ADC units $54_1$, $54_2$, $54_3$, $54_N$, and sensor interface 56 are provided to create signals indicative of characteristics of the field for P&O determination. The transmitter interface 42 is connected to the location and orientation processor 40 and to the look-up table units $44_1$, $44_2$, $44_3$. The DAC units $46_1$, $46_2$, $46_3$ are connected to a respective ones of the look-up table units $44_1$, $44_2$, $44_3$ and to the amplifier 48, which is further connected to the transmitter 50. The transmitter 50 may be coupled to a portion of the operating environment (e.g., to an imaging apparatus, such as a C-arm 26, as shown in FIG. 2, or to a patient bed). The analog to digital converters (ADC) $54_1$, $54_2$, $54_3$, $54_N$ are respectively connected to the sensors $52_1$, $52_2$, $52_3$, $52_N$ and to the sensor interface 56, which is further connected to location and orientation processor 40.

Each of the look-up table units $44_1$, $44_2$, $44_3$ may produce a cyclic sequence of numbers and provide it to a respective DAC unit $46_1$, $46_2$, $46_3$, which in turn may translate the respective sequence to a respective analog signal. Each of the analog signals may be respective of a different spatial axis. In the present example, a first look-up table $44_1$ and DAC unit $46_1$ produce a signal for the X axis, a second look-up table $44_2$ and DAC unit $46_2$ produce a signal for the Y axis, and a third look-up table $44_3$ and DAC unit $46_3$ may produce a signal for the Z axis.

The DAC units $46_1$, $46_2$, $46_3$ provide their respective analog signals to the amplifier, which amplifies and provides the amplified signals to the transmitter. The transmitter may provide a multiple axis electromagnetic field, which can be detected by the MPS sensors $52_1$, $52_2$, $52_3$, $52_N$. Each of the MPS sensors $52_1$, $52_2$, $52_3$, $52_N$ may be configured to detect an electromagnetic field, produce a respective electrical analog signal, and provide the analog signal to a respective ADC unit $54_1$, $54_2$, $54_3$, $54_N$. Each of the ADC units $54_1$, $54_2$, $54_3$, $54_N$ may digitize the analog signal fed thereto, convert it to a sequence of numbers, and provide the sequence to the sensor interface 56, which in turn may provide it to the location and orientation processor 40. The location and orientation processor 40 may analyze the received sequences of numbers, thereby determining the location and orientation of each of the MPS sensors $52_1$, $52_2$, $52_3$, $52_N$. The location and orientation processor 40 may further determine distortion events and update the look-up tables $44_1$, $44_2$, $44_3$ accordingly. Referring to FIGS. 1-3, the functionality and/or hardware of the location and orientation processor 40, the magnetic processing core 34, and/or in the control unit 12 may be combined in a single apparatus, or may be distributed among several apparatus.

The MPS 18 may compensate for respiration-induced and other patient body motion, substantially as described in U.S. patent application Ser. No. 12/650,932 (published as United States patent application publication 2011/0158488), which is hereby incorporated by reference in its entirety. One of MPS sensors $52_1$, $52_2$, $52_3$, $52_N$ may be a patient reference sensor (PRS) configured to provide a stable positional reference on the patient's body for such motion compensation. The PRS may be attached to the patient's manubrium sternum or another location.

Referring again to FIG. 1, the system 10 may find use in developing and outputting a cine-loop for viewing on the display 16 by a physician during a medical procedure. A "good" cine-loop may include an accurate representation of the anatomy of interest throughout the cine-loop. Thus, a "good" cine-loop may show an image that is close to a snapshot of the anatomy as it will be in the near future or was in the near past. The geometry of many organs, such as the heart, changes over the course of time due to various physiological reasons. For the heart, for example, heart contraction and respiration both cause position and shape changes in the heart over time, impacting how the heart should and/or does appear in an image. A "bad" cine-loop replay may show an atypical image that is not representative of an actual snapshot of the near present.

A challenge in developing a cine-loop is to generate one that is representative of the entire medical procedure, so when played, it will resemble the actual movement of the organ at all stages of the medical procedure. One way of accomplishing this goal is by producing a cine-loop that represents a normal or ideal sequence. If a recorded image includes an atypical event, that image may be removed (i.e., set aside or cropped) from the cine-loop, as detailed in the methods below.

Figure 4:
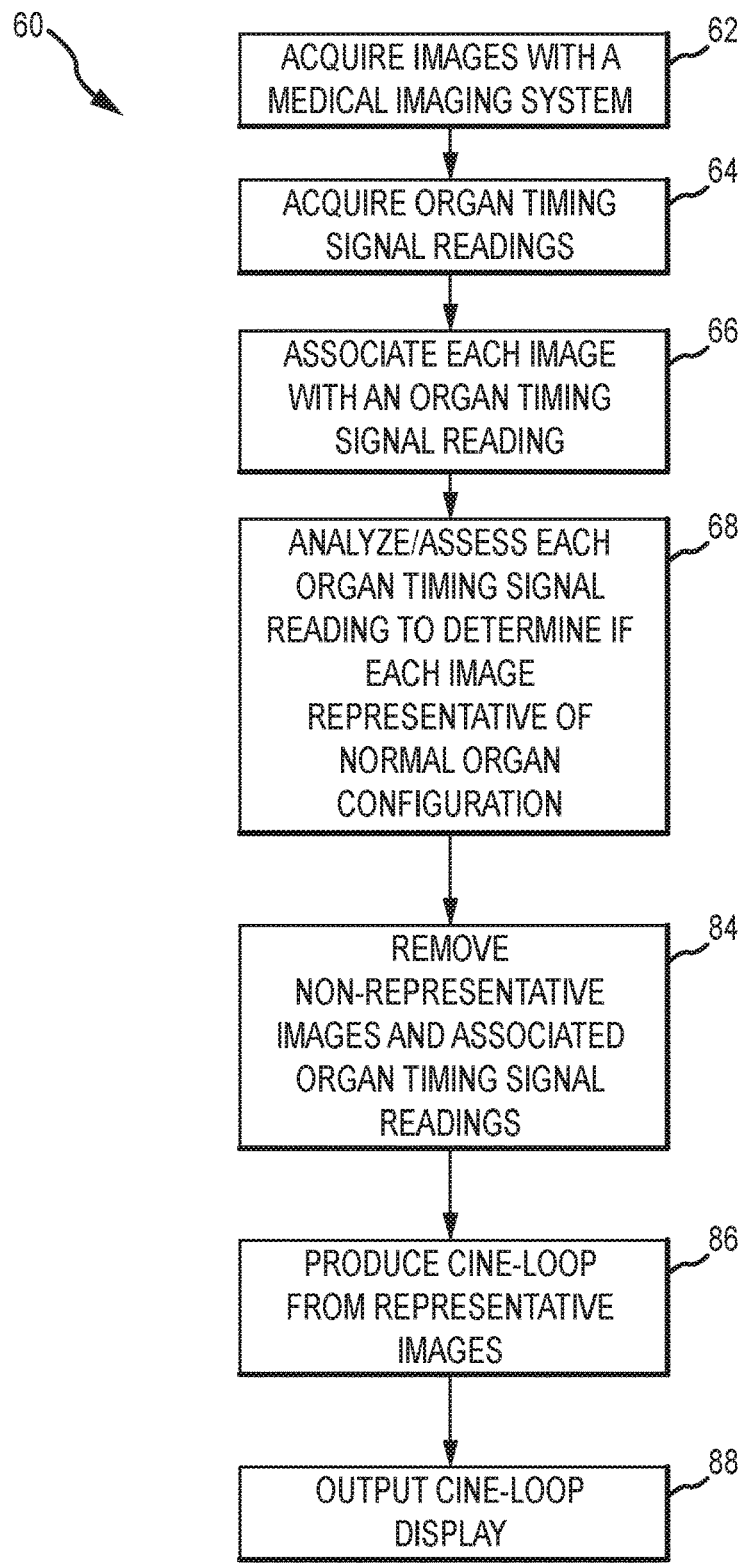
FIG. 4 is a flow chart illustrating an exemplary method of emulating prerecorded images of an organ.

FIG. 4 is a flow chart illustrating a method 60 for emulating prerecorded images, such as images of an organ. The emulated images may take the form of a cine-loop, as described below. The following description of the method 60 will be with reference to an embodiment in which the organ of interest is a heart, but it should be understood that the method 60 may also find use with organs in addition to or other than the heart, in embodiments.

The emulation method 60 may begin with a step 62 of acquiring a plurality of images with a medical imaging system and a step 64 of acquiring organ timing signal readings, each representing an activity state of the organ, with an organ timing signal detector. In embodiments, the organ timing signal detector may be an ECG system 20, the organ timing signal readings may be portions of an ECG, and the medical imaging system 14 may be a fluoroscopy system, as shown in and described with respect to FIGS. 1 and 2.

The acquired images may be collected at a plurality of different activity states of the heart (i.e., portions of a cardiac cycle). Accordingly, the method 60 may include an associating step 66 that involves associating each image with one of the acquired organ timing signal readings (i.e., with an activity state of the heart according to a respective portion of the acquired ECG, as well as with the specific reading or portion of the organ timing signal).

In an embodiment, the associating step 66 may further include associating each image with an anatomy configuration type (i.e., patient body position) and/or system accuracy grade (i.e., an ability of the system to overlay or superimpose a representation of a medical device on the captured image). System accuracy grade may be affected by, for example only, sensor fault, unexpected patient movement, unexpected imaging system movement, and other factors influencing the quality of an image or the similarity of an image frame to other images.

The method 60 may also include an analysis step 68 that involves analyzing or assessing each associated image and organ timing signal reading to determine if the image is representative of a normal configuration of the organ at the activity state. An image may be non-representative if, for example, it was captured when the organ had an atypical shape and/or position for the activity state based on the organ timing signal. For example, non-representative images of a heart may be due to premature ventricular contraction (PVC), ventricular tachycardia, paroxysmal supra-ventricular tachycardia, and other arrhythmia.

The analysis step 68 may comprise, for each acquired image, analyzing the organ timing signal reading (e.g., ECG portion) associated with that image. The organ timing signal reading may include indications of atypical activity of the organ (e.g., arrhythmia of the heart), and the analysis step may include processing the organ timing signal reading to check for such features.

Figure 5:
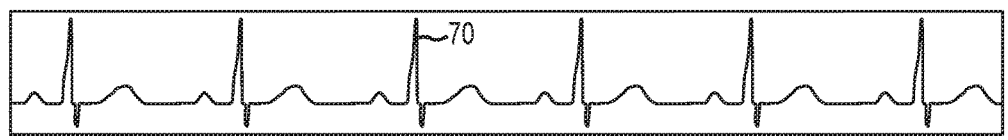
FIG. 5 is a plot of an electrocardiogram (ECG) in sinus mode or rhythm.
Figure 6:
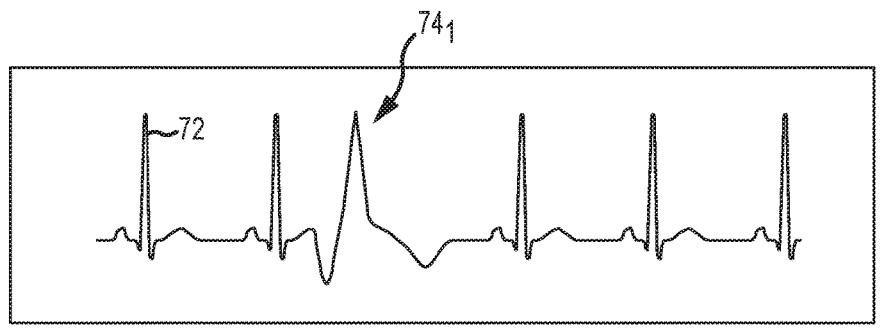
FIG. 6 depicts an ECG plot including a premature ventricular contraction (PVC) episode.
Figure 7:
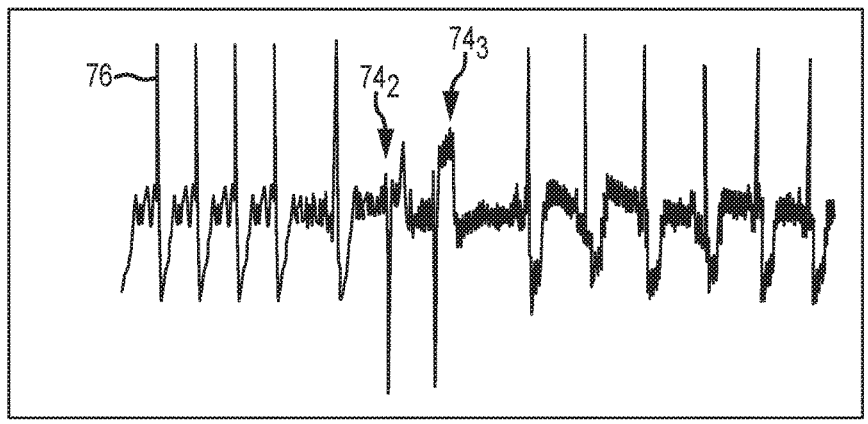
FIG. 7 depicts a plot of various data including PVC episodes during a cine capture.
Figure 8:
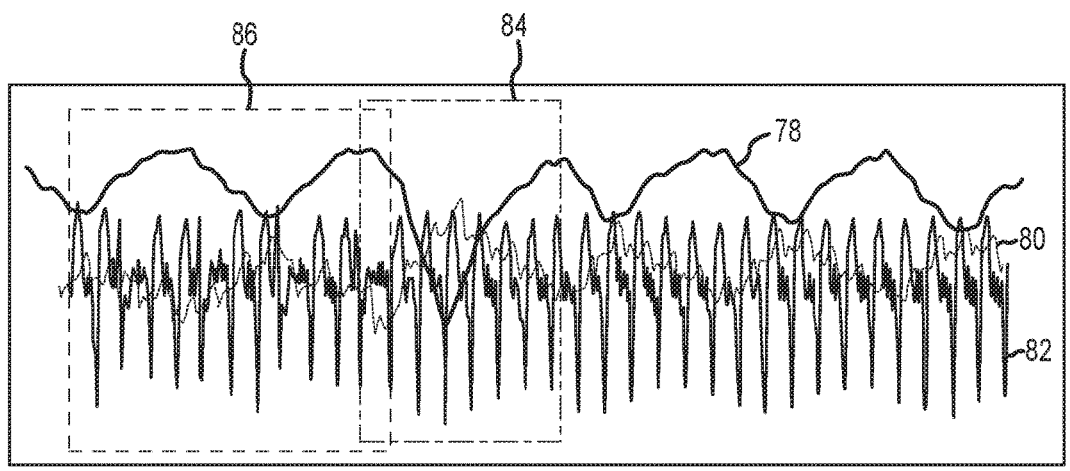
FIG. 8 depicts a plot of respiration, organ state, and ECG data during a cine capture and highlighting two areas which may be used to remove correlating images from an image set.

FIGS. 5-8 illustrate plots of various organ timing signals that may be processed and analyzed to determine if images associated with portions of those organ timing signals are representative of a normal configuration of an organ. FIG. 5 is a plot of an electrocardiogram (ECG) 70 in sinus mode or rhythm. FIG. 6 depicts an ECG plot 72 including a premature ventricular contraction (PVC) episode $74_1$. FIG. 7 depicts a plot of an organ timing signal 76, including PVC episodes $74_2$, $74_3$. FIG. 8 depicts a plot of respiration 78, organ state 80, and ECG data 82 during a cine capture and highlighting two areas 84, 86 which may be used to remove correlating images from an image set.

Referring to FIGS. 4-8, the analysis step 68 may include analyzing portions/readings of one or more organ timing signals 70, 72, 76, 78, 80, 82 to determine if the signals 70, 72, 76, 78, 80, 82 include indications of atypical organ configuration. Such indications include, but are not limited to, the signal portions $74_1$, $74_2$, $74_3$ related to PVC episodes indicated in the organ timing signals 72, 76 in FIGS. 5 and 6 and the signal abnormalities of areas 84, 86 in FIGS. 7 and 8, which may be found by analyzing various aspects of the organ timing signals 70, 72, 76, 78, 80, 82. For example, but without limitation, the morphology (e.g., amplitude, edge sharpness, slope, etc.), energy, and/or other characteristics of an organ timing signal 70, 72, 76, 78, 80, 82 may be compared to normal or ideal signals (i.e., the organ timing signal portion or organ timing signal reading associated with an image may be compared to a normal or ideal signal portion or reading for the organ timing state with which the image and signal portion or reading are associated). In an embodiment in which an ECG 70, 72, 82 is used as an organ timing signal, the comparison may be made to a normal or ideal QRS shape (i.e., or a portion of a normal or ideal QRS shape). If an organ timing signal portion or reading is sufficiently similar to the normal or ideal, then the image associated with that organ timing signal or portion may be considered representative of the normal organ configuration for the organ activity state with which the image and signal portion or reading are associated. If an organ timing signal or portion may be considered representative of some non-normal or non-ideal configuration (such as, for example, as a result of arrhythmia), the image associated with that organ timing signal or portion may be considered non-representative of the normal organ configuration, and may instead be considered representative of an abnormal configuration.

After each image is analyzed or assessed at the analysis step, non-representative images and organ timing signal readings associated with those images may be removed at a removing step 84. At a production step 86, representative images may be used to produce a cine-loop, substantially as described in U.S. patent application Ser. No. 09/782,528 (issued as U.S. Pat. No. 7,386,339), U.S. application Ser. No. 11/841,451 (issued as U.S. Pat. No. 7,697,973), U.S. application Ser. No. 11/233,420 (published as United States patent application publication No. 2006/0058647), U.S. application Ser. No. 12/941,514 (published as United States patent application publication No. 2011/0054308), U.S. application Ser. No. 11/233,948 (issued as U.S. Pat. No. 7,840,252), U.S. application Ser. No. 11/815,154 (published as United States patent application publication No. 2008/0319312), U.S. application Ser. No. 13/339,588, and international application No. PCT/IB2011/055954 (published as international publication No. WO 2012/090148), all of which are hereby incorporated by reference as though fully set forth herein. As detailed in the above-incorporated references, the cine-loop may include a series of images, based on or including the representative images, arranged in sequence to emulate the appearance of the organ over the course of one or more cyclic periods (e.g., a heart over one or more cardiac cycles).

The method 60 may further include an output step 88 that involves outputting the cine-loop for a display. The cine-loop may be displayed, as detailed in the above-incorporated references, as a continuous loop of the same set of images, output and displayed in synchronization with a real-time organ timing signal. Accordingly, a cine-loop based on the representative images may be repeatedly shown, with a representation of a medical device superimposed on the images, in an embodiment. Portions of the cine-loop displaying an emulation of the organ during a given portion of an organ timing signal may be based on the images associated with that portion of the organ timing signal.

In summary, the method 60 generally includes steps for acquiring a plurality of images of an organ (e.g., a heart), removing those images determined to be non-representative of an expected configuration (e.g., shape and/or position) of the organ, and creating and outputting a cine-loop based only on representative images. The method 60 may improve on known systems and methods by not basing the cine-loop on images collected at a time when the organ has a non-representative configuration. Accordingly, a cine-loop produced and output according to the method 60 may be more accurate than cine-loops produced and output according to known methods.

Referring to FIGS. 1 and 4, the control unit 12 may be configured to perform one or more steps and/or portions of steps of the method 60. That is, the memory 22 may include instructions such that, when executed by the processor 24, the control unit 12 performs one or more steps and/or portions of steps of the method 60.

Figure 9:
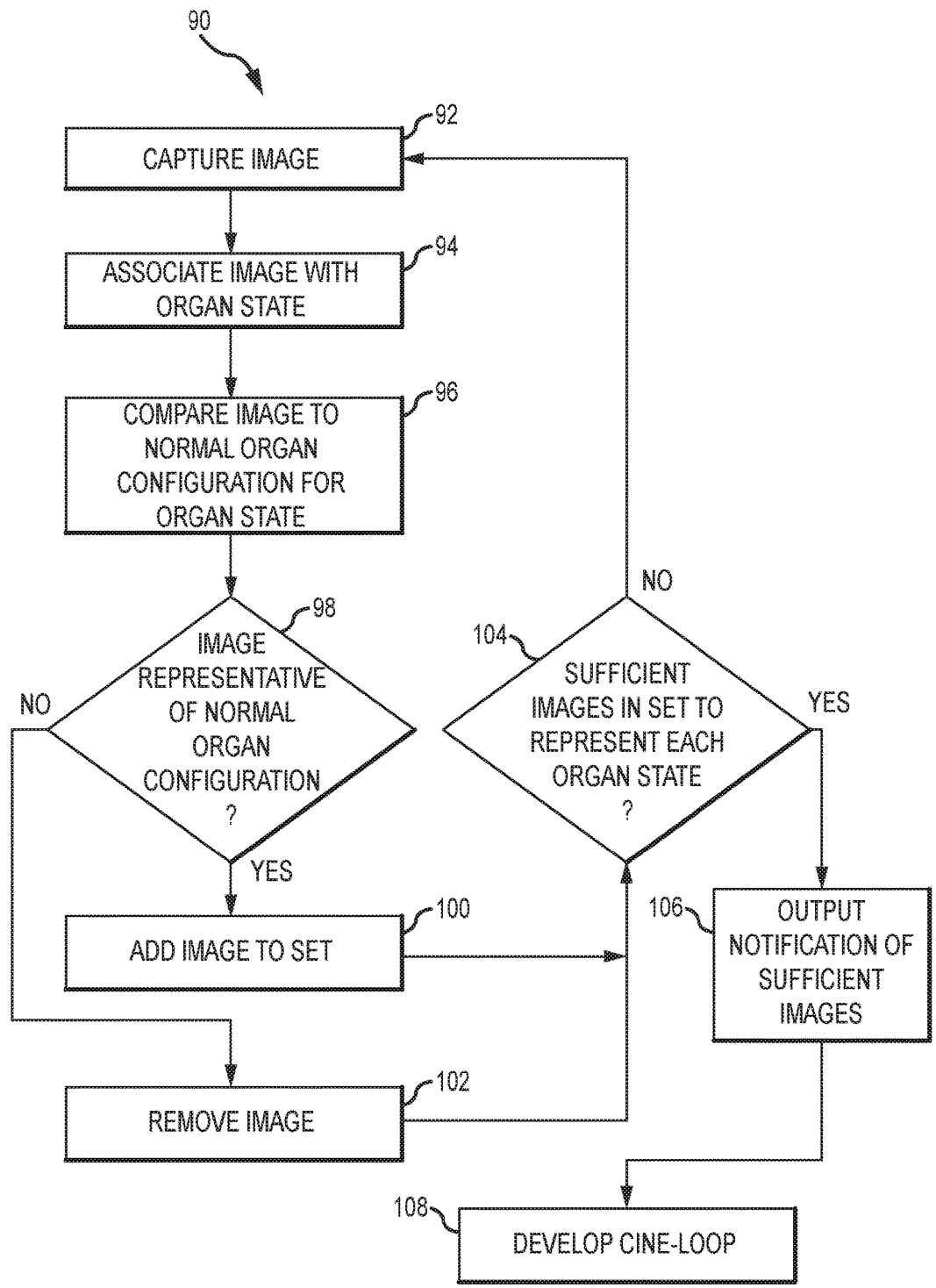
FIG. 9 is a flow chart illustrating an exemplary method of producing a cine-loop of an organ.

The control unit 12 may also be configured to direct (i.e., perform one or more steps of a method for) the collection of images for the creation or production of a cine-loop. FIG. 9 is a flow chart illustrating exemplary steps of such a method 90. Referring to FIGS. 1 and 9, the method 90 may include an image capture step 92 that includes capturing an image with, for example, the medical imaging system 14. The image may be captured responsive to a physician's press of a foot pedal, for example. The image may also be captured as part of an automated process (e.g., directed by the control unit).

At an association step 94, the captured image may be associated with an organ activity state. The organ activity state may be determined according to an organ timing signal, such as an ECG from the ECG system 20. The association step 94 may further include associating the captured image with an organ timing signal portion or reading, such as a portion of reading of an ECG from the ECG system 20.

A comparison step 96 may involve comparing the image, or data associated with the image, to a normal configuration of the organ for the activity state with which the image is associated. The comparison step 96 may include, in an embodiment, comparing the organ timing signal portion or reading to a normal or ideal organ timing signal portion or reading. This comparison may include, in embodiments, analyzing the morphology, energy, and/or other characteristics of the organ timing signal portion or reading and comparing it with the morphology, energy, and/or other characteristics of a normal or ideal organ timing signal portion or reading.

The comparison step 96 may be performed in conjunction with a first query step 98, in which it is determined whether the image is representative of the organ configuration expected at the activity state with which the image is associated. If the image is representative (e.g., based on a comparison of an organ timing signal portion or reading with an expected or ideal organ timing signal portion or reading, as described above), the image may be added to an image set at an image addition step 100. If not, the image may be removed at a removing step 102. The removing step may involve, in an embodiment, setting aside the removed image for use in a non-representative cine-loop or other purpose. For example, as noted above, an image may be representative of abnormal behavior, and may be used for a cine-loop illustrating that abnormal configuration.

After the addition and removing steps 100, 102, at a second query step 104, it may be determined if the image set includes sufficient images to represent the organ in every activity state of the organ. In an embodiment of the method in which the organ of interest is the heart, the second query step 104 may involve determining if the image set includes sufficient images to represent the heart throughout a cardiac cycle—i.e., sufficient images for a cine-loop of the heart for a cardiac cycle.

If there are not sufficient images, the capture step 92, associate step 94, comparison step 94, and first query, addition, and removing steps 98, 100, 102 may be repeated as many times as are necessary to have sufficient representative images. If there are sufficient images, a notification step 106 may be performed that includes outputting a notification that sufficient images have been collected. The notification may be visual, audible, and/or some other known output means. The notification may notify a physician, in an embodiment, that a foot pedal used to capture images with the medical imaging system may be released. In another embodiment, the notification step 106 may further include automatically disabling image capture.

The method 90 may further include a production step 108 that involves producing a cine-loop based on the images that are determined to be representative (i.e., the images added to the image set in the addition step). As noted above, the cine-loop may be produced according to known methods described in one or more of in U.S. patent application Ser. No. 09/782,528 (issued as U.S. Pat. No. 7,386,339), U.S. application Ser. No. 11/841,451 (issued as U.S. Pat. No. 7,697,973), U.S. application Ser. No. 11/233,420 (published as United States patent application publication No. 2006/0058647), U.S. application Ser. No. 12/941,514 (published as United States patent application publication No. 2011/0054308), U.S. application Ser. No. 11/233,948 (issued as U.S. Pat. No. 7,840,252), U.S. application Ser. No. 11/815,154 (published as United States patent application publication No. 2008/0319312), U.S. application Ser. No. 13/339,588, and international application No. PCT/IB2011/055954 (published as international publication No. WO 2012/090148).

The method 90 may improve upon known procedures by minimizing the amount of images captured for the development of a cine-loop, which may minimize imaging radiation exposure for both a patient and a physician.

Although a number of embodiments have been described above with a certain degree of particularity, those skilled in the art could make numerous alterations to the disclosed embodiments without departing from the sprit or scope of this disclosure. For example, all joinder referenced (e.g., attached, coupled, connected, and the like) are to be construed broadly and may include intermediate members between a connection of elements and relative movement between elements. As such, joined references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by referenced herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A control unit for a system for displaying looped images, the control unit configured to be coupled with a medical imaging system, the control unit comprising:

a computer-readable memory configured to store instructions; and a processor configured to execute the instructions to:
associate each of a plurality of two dimensional images of an organ acquired from the medical imaging system with a respective organ timing signal portion, wherein each respective organ timing signal portion represents an activity state of the organ;
determine one or more characteristics of each respective organ timing signal portion;
assess one or more of the characteristics to determine whether one or more of the plurality of two dimensional images is representative of a normal configuration of the organ at the respective activity state; and
output, for a display, a set of looped images that comprises each of the plurality of two-dimensional images that is representative of the normal configuration of the organ at the respective activity state and excludes each of the plurality of two-dimensional images that is not representative of the normal configuration of the organ at the respective activity state.

2. The control unit of claim 1, wherein the organ timing signal portion comprises at least a portion of an electrocardiogram or a respiratory signal.

3. The control unit of claim 1, wherein the activity state of the organ comprises at least a portion of a cycle of the organ.

4. The control unit of claim 1, wherein the one or more characteristics comprises a morphology or an energy of each respective organ timing signal portion.

5. The control unit of claim 4, wherein the morphology comprises one or more of an amplitude, an edge sharpness, and a slope of each respective organ timing signal portion.

6. The control unit of claim 1, wherein the organ is a heart, and a two-dimensional image of the plurality of two-dimensional images that is not representative of the normal configuration of the organ at the respective activity state is indicative of at least one of:
premature ventricular contraction;
ventricular tachycardia;
paroxysmal supra-ventricular tachycardia; and
another heart arrhythmia.

7. The control unit of claim 1, wherein the organ is a heart, and the normal configuration of the heart at each respective activity state is associated with a normal cardiac rhythm.

8. The control unit of claim 1, wherein the control unit is further configured to be coupled with an organ timing signal detector and the processor is configured to execute the instructions to further:
output the set of looped images substantially in synchronization with a real-time organ timing signal obtained from the organ timing signal detector.

9. The control unit of claim 1, wherein the organ timing signal portion comprises at least a portion of an electrocardiogram, and wherein the processor is configured to assess one or more of the characteristics of the electrocardiogram portion by comparing the electrocardiogram portion to a normal or ideal QRS shape.

10. A method for emulating prerecorded images comprising:
acquiring at least one organ timing signal reading representing an activity state of an organ with at least one organ timing signal detector;
acquiring a plurality of images with a medical imaging system;
associating each of the plurality of images with an organ timing signal reading;

determining a respective characteristic for each organ timing signal reading;

assessing one or more of the respective characteristics to determine whether one or more of the plurality of images is representative of a normal configuration of the organ at the respective activity state;

removing any of the organ timing signal readings and associated images that are not representative of the normal organ configuration; and outputting a sequence of the representative images for a display.

11. The method of claim 10, wherein the at least one organ timing signal reading is an electrocardiogram or a respiratory signal.

12. The method of claim 10, wherein the activity state of the organ comprises at least a portion of a cycle of the organ.

13. The method of claim 10, wherein the respective characteristic comprises a morphology or an energy of each organ timing signal reading.

14. The method of claim 13, wherein the morphology comprises one or more of an amplitude, an edge sharpness, and a slope of each respective organ timing signal reading.

15. The method of claim 10, wherein the removing step is in accordance with a QRS shape of the organ timing signal reading.

16. A system for emulating prerecorded images, comprising:

at least one organ timing signal detector configured to acquire at least one organ timing signal reading, said organ timing signal reading representing an activity state of an organ;

a medical imaging system for acquiring a plurality of images; and a control unit, coupled with the organ timing signal detector and with the medical imaging system, wherein the control unit is configured to:

associate each of the plurality of images with a respective organ timing signal reading;

determine a respective characteristic for each organ timing signal reading;

assess one or more of the respective characteristics to determine whether one or more of the plurality of images is representative of a normal configuration of the organ at the respective activity state;

produce only representative images by analyzing the at least one organ timing signal reading and removing any of the organ timing signals readings and the associated images that do not conform to a representative organ state; and send only representative images to a display system by corresponding the associated images with the conforming organ timing signal readings.

17. The system of claim 16, wherein the medical imaging system comprises a fluoroscope.

18. The system of claim 16, wherein the organ timing signal reading comprises at least a portion of an electrocardiogram or a respiratory signal.

19. The system of claim 16, wherein the activity state of the organ comprises at least a portion of a cycle of the organ.

20. The system of claim 16, wherein the characteristic comprises a morphology or an energy of each respective organ timing signal reading.

21. The system of claim 20, wherein the morphology comprises one or more of an amplitude, an edge sharpness, and a slope of each respective organ timing signal portion.

22. The system of claim 16, wherein the control unit is further configured to direct a process of acquiring the plurality of images by providing an indication of whether a sufficient number of images has been collected to represent the organ over a complete cycle of the organ timing signal.

23. The system of claim 16, wherein the control unit is further configured to superimpose a representation of a medical device on the representative images.

24. The system of claim 16, wherein the control unit is further configured to send the representative images to be displayed in a continuous loop.

25. The system of claim 24, wherein the loop is synchronized with the organ timing signal readings in real time.

* * * * *